US012662585B2

(12) United States Patent
Hwang et al.

(10) Patent No.: US 12,662,585 B2
(45) Date of Patent: Jun. 23, 2026

(54) METHOD FOR PRODUCING POLYESTER RESIN BY USING REGENERATED BIS(2-HYDROXYETHYL) TEREPHTHALATE AQUEOUS SOLUTION

(71) Applicant: SK CHEMICALS CO., LTD., Gyeonggi-do (KR)

(72) Inventors: Da-Young Hwang, Gyeonggi-do (KR); Ha-Neul Kim, Gyeonggi-do (KR); Yoo Jin Lee, Gyeonggi-do (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 107 days.

(21) Appl. No.: 18/708,602

(22) PCT Filed: Apr. 26, 2023

(86) PCT No.: PCT/KR2023/005653
§ 371 (c)(1),
(2) Date: May 9, 2024

(87) PCT Pub. No.: WO2023/214727
PCT Pub. Date: Nov. 9, 2023

(65) Prior Publication Data

US 2025/0382433 A1 Dec. 18, 2025

(30) Foreign Application Priority Data

May 4, 2022 (KR) ........................ 10-2022-0055673

(51) Int. Cl.

| | |
|---|---|
| ***C08J 11/24*** | (2006.01) |
| ***C07C 67/03*** | (2006.01) |
| ***C07C 67/08*** | (2006.01) |
| ***C07C 67/54*** | (2006.01) |
| ***C07C 67/56*** | (2006.01) |
| ***C08G 63/183*** | (2006.01) |
| ***C08G 63/19*** | (2006.01) |
| ***C08G 63/199*** | (2006.01) |
| ***C08G 63/42*** | (2006.01) |
| ***C08G 63/60*** | (2006.01) |
| ***C08G 63/672*** | (2006.01) |
| ***C08G 63/85*** | (2006.01) |
| ***C08G 63/91*** | (2006.01) |

(52) U.S. Cl.
CPC ............... *C08J 11/24* (2013.01); *C07C 67/03* (2013.01); *C07C 67/08* (2013.01); *C07C 67/54* (2013.01); *C07C 67/56* (2013.01); *C08G 63/183* (2013.01); *C08G 63/19* (2013.01); *C08G 63/199* (2013.01); *C08G 63/42* (2013.01); *C08G 63/60* (2013.01); *C08G 63/672* (2013.01); *C08G 63/85* (2013.01); *C08G 63/916* (2013.01); *C08J 2367/00* (2013.01)

(58) Field of Classification Search
USPC ........................................................ 521/48.5
See application file for complete search history.

(56) References Cited

U.S. PATENT DOCUMENTS

| | | | |
|---|---|---|---|
| 6,642,350 B1 | 11/2003 | Asakawa et al. | |
| 7,211,193 B2 | 5/2007 | Inada et al. | |

FOREIGN PATENT DOCUMENTS

| | | | | | |
|---|---|---|---|---|---|
| JP | S50-029459 B1 | | 9/1975 | |
| JP | 2003055300 A | * | 2/2003 | .............. C08J 11/24 |
| JP | 2009-173732 A | | 8/2009 | |
| KR | 10-1386683 B1 | | 4/2014 | |
| KR | 10-2021-0067554 A | | 6/2021 | |
| KR | 10-2022-0055192 A | | 5/2022 | |
| KR | 20220055192 A | * | 5/2022 | ............. C08G 63/60 |
| WO | 2021/124149 A1 | | 6/2021 | |
| WO | 2022/108071 A1 | | 5/2022 | |

OTHER PUBLICATIONS

JP-2003055300-A Machine Translation (Year: 2003).*
KR-20220055192-A Machine Translation (Year: 2022).*
Sang Ho Park et al., Poly (ethylene terephthalate) recycling for high value added textiles, Fashion and Textiles, 2014, p. 1-17, 1:1.
International Search Report for the International Application No. PCT/KR2023/005653 issued by the International Searching Authority (Korean Patent Office) on Jul. 31, 2023.
Extended European Search Report for European Patent Application No. 23799610.3 issued by the European Patent Office on Dec. 1, 2025.

* cited by examiner

*Primary Examiner* — Terressa Boykin
(74) *Attorney, Agent, or Firm* — IP & T GROUP LLP

(57) ABSTRACT

A regenerated bis(2-hydroxyethyl) terephthalate obtained by the depolymerization of waste polyester is mixed with water to prepare an aqueous solution under specific temperature and concentration conditions, thereby ensuring storage stability. By introducing such a regenerated bis(2-hydroxyethyl) terephthalate aqueous solution into the polymerization of a polyester resin, the uniformity of raw materials and reaction efficiency can be increased, thereby improving the quality of the final polyester resin.

13 Claims, 1 Drawing Sheet

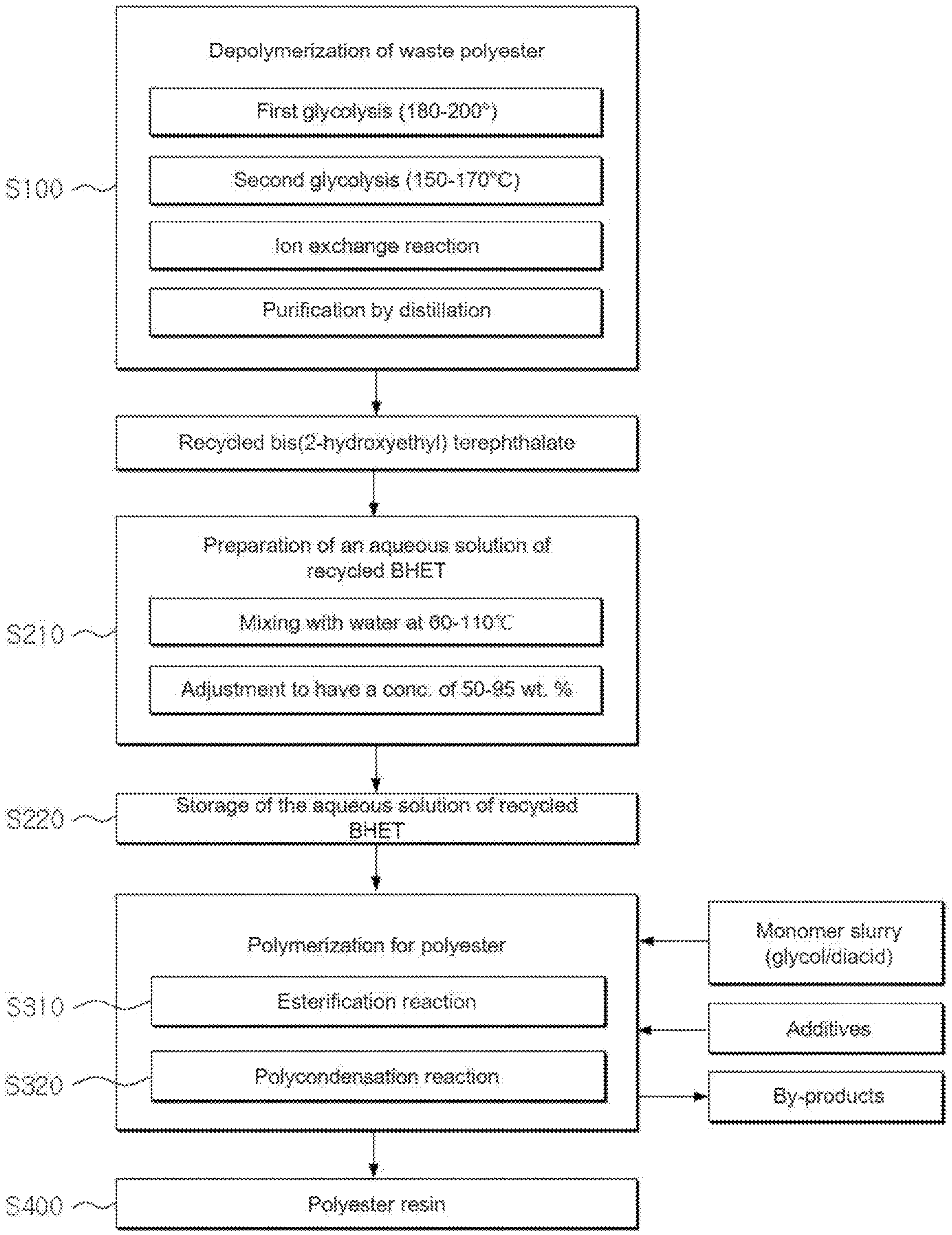
Depolymerization of waste polyester
First glycolysis (180-200°)
Second glycolysis (150-170°C)
Ion exchange reaction
Purification by distillation
S100
Recycled bis(2-hydroxyethyl) terephthalate
Preparation of an aqueous solution of recycled BHET
Mixing with water at 60-110℃
Adjustment to have a conc. of 50-95 wt. %
S210
Storage of the aqueous solution of recycled BHET
S220
Polymerization for polyester
Esterification reaction
Polycondensation reaction
S310
S320
Monomer slurry (glycol/diacid)
Additives
By-products
Polyester resin
S400

METHOD FOR PRODUCING POLYESTER RESIN BY USING REGENERATED BIS(2-HYDROXYETHYL) TEREPHTHALATE AQUEOUS SOLUTION

This application is a national stage application of PCT/KR2023/005653 filed on Apr. 26, 2023, which claims priority to Korean Patent Application No. 10-2022-0055673 filed on May 4, 2022. The disclosure of each of the foregoing applications is incorporated herein by reference in its entirety.

TECHNICAL FIELD

The present invention relates to an aqueous solution of recycled bis(2-hydroxyethyl) terephthalate and to a process for preparing a polyester resin using the same.

BACKGROUND ART

Polyester is widely used as a material for beverage-filling containers, packaging films, audio and video films, and the like by virtue of its excellent mechanical strength, thermal resistance, transparency, and gas barrier properties. In addition, polyester is widely produced worldwide as an industrial material such as medical fibers and tire cords. In particular, polyester sheets or plates have good transparency and excellent mechanical strength, so that they are widely used as raw materials for cases, boxes, partitions, shelves, panels, packaging materials, building materials, interior and exterior materials, and the like.

As a result, waste of plastics such as polyester is generated globally at an unmanageable level every year. Recently, countries around the world are preparing regulations and plans for recycling waste plastic resources, including waste polyester. For example, there is an attempt to use a recycled resin in packaging materials used in various fields at a certain ratio or more. Although physical or chemical methods are used as methods of recycling waste polyester, physical recycling methods cannot guarantee purity and are not widely used.

In chemical recycling methods, the ester bond of waste polyester is cleaved to depolymerize it. Reactions such as glycolysis, hydrolysis, methanolysis, and aminolysis are used. Glycolysis among them is to decompose waste polyester by adding a glycol such as ethylene glycol or diethylene glycol at high temperatures. A reaction product containing mainly bis(2-hydroxyethyl) terephthalate (BHET) is obtained. The bis(2-hydroxyethyl) terephthalate may be used as a raw material for preparing unsaturated polyester or ester polyol after the crystallization or purification thereof.

PRIOR ART DOCUMENT (Patent Document 1) Korean Patent No. 1386683
(Patent Document 02) U.S. Pat. No. 7,211,193
(Non-patent Document 1) Park, S. H., Kim, S. H., Poly (ethylene terephthalate) recycling for high value added textiles, Fashion and Textiles 1, 1 (2014)

DISCLOSURE OF INVENTION

Technical Problem

Recycled bis(2-hydroxyethyl) terephthalate obtained through the depolymerization of waste polyester may be thereafter stored for a period of time before being put into the polymerization of a polyester resin. The quality of recycled BHET may deteriorate depending on the storage conditions during this period, in which case the quality of a final polyester resin may be affected.

As a result of the study conducted by the present inventors, it has been discovered that, when recycled bis(2-hydroxyethyl) terephthalate is mixed with water to prepare an aqueous solution under specific temperature and concentration conditions, storage stability can be secured and that the uniformity of a raw material and the reaction efficiency can be enhanced by introducing the aqueous solution of recycled BHET into the polymerization for a polyester resin.

Accordingly, an object of the present invention is to provide a process for preparing an aqueous solution of recycled bis(2-hydroxyethyl) terephthalate having excellent storage stability and a process for preparing a polyester resin with high quality using the same.

Solution to Problem

According to the present invention, there is provided a process for preparing a polyester resin, which comprises (1) depolymerizing waste polyester to prepare recycled bis(2-hydroxyethyl) terephthalate; (2) mixing the recycled bis(2-hydroxyethyl) terephthalate with water at 60° C. to 110° C. to prepare an aqueous solution of recycled bis(2-hydroxyethyl) terephthalate having a concentration of 50% by weight to 95% by weight; and (3) preparing a polyester resin through an esterification reaction and a polycondensation reaction using the aqueous solution of recycled bis(2-hydroxyethyl) terephthalate.

In addition, according to the present invention, there is provided a process for preparing an aqueous solution of recycled bis(2-hydroxyethyl) terephthalate, which comprises (1) depolymerizing waste polyester to prepare recycled bis(2-hydroxyethyl) terephthalate; and (2) mixing the recycled bis(2-hydroxyethyl) terephthalate with water at 60° C. to 110° C. to prepare an aqueous solution thereof having a concentration of 50% by weight to 95% by weight.

Advantageous Effects of Invention

According to the present invention, when recycled bis(2-hydroxyethyl) terephthalate obtained through the depolymerization of waste polyester is mixed with water to prepare an aqueous solution under specific temperature and concentration conditions, storage stability can be secured, and the uniformity of a raw material and the reaction efficiency can be enhanced by introducing the aqueous solution of recycled BHET into the polymerization for a polyester resin.

Specifically, the aqueous solution of recycled BHET shows very little change in purity and color even after storage for a certain period of time, and a polyester resin polymerized using the aqueous solution of recycled BHET also has excellent color quality. Accordingly, the polyester resin of the present invention can be used in the preparation of articles made of environmentally friendly materials in various fields.

BRIEF DESCRIPTION OF DRAWINGS

FIG. 1 illustrates the process for preparing an aqueous solution of recycled bis(2-hydroxyethyl) terephthalate according to an embodiment and for preparing a polyester resin using the same.

BEST MODE FOR CARRYING OUT THE INVENTION

Hereinafter, the present invention will be described in more detail.

In this specification, terms referring to the respective components are used to distinguish them from each other and are not intended to limit the scope of the embodiment. In addition, in the present specification, a singular expression is interpreted to cover a plural number as well unless otherwise specified in the context.

In the present specification, the terms first, second, and the like are used to describe various components. But the components should not be limited by the terms. The terms are used for the purpose of distinguishing one element from another.

In the present specification, the term "comprising" is intended to specify a particular characteristic, region, step, process, element, and/or component. It does not exclude the presence or addition of any other characteristic, region, step, process, element and/or component, unless specifically stated to the contrary.

According to an aspect of the present invention, there is provided a process for preparing a polyester resin, which comprises (1) depolymerizing waste polyester to prepare recycled bis(2-hydroxyethyl) terephthalate; (2) mixing the recycled bis(2-hydroxyethyl) terephthalate with water at 60° C. to 110° C. to prepare an aqueous solution of recycled bis(2-hydroxyethyl) terephthalate having a concentration of 50% by weight to 95% by weight; and (3) preparing a polyester resin through an esterification reaction and a polycondensation reaction using the aqueous solution of recycled bis(2-hydroxyethyl) terephthalate.

According to another aspect of the present invention, there is provided a process for preparing an aqueous solution of recycled bis(2-hydroxyethyl) terephthalate, which comprises (1) depolymerizing waste polyester to prepare recycled bis(2-hydroxyethyl) terephthalate; and (2) mixing the recycled bis(2-hydroxyethyl) terephthalate with water at 60° C. to 110° C. to prepare an aqueous solution thereof having a concentration of 50% by weight to 95% by weight.

FIG. 1 illustrates the process for preparing a polyester resin using an aqueous solution of recycled bis(2-hydroxyethyl) terephthalate according to an embodiment.

Referring to FIG. 1, first, high-purity regenerated BHET is obtained through a depolymerization step (S100), in which waste polyester is crushed into flakes, and a two-stage glycolysis reaction (180 to 200° C. and 150 to 170° C.) is carried out, followed by purification through ion exchange and distillation. Thereafter, the recycled BHET is mixed with water at 60 to 110° C., and water is further added thereto, or evaporated therefrom, to prepare an aqueous solution in which the concentration is adjusted to 50 to 95% by weight (S210). The aqueous solution of recycled BHET is stored until it is introduced into the polymerization for a polyester resin (S220). Thereafter, in the polymerization for a polyester resin, the aqueous solution of recycled BHET is fed to a reactor with an additive, and, optionally, an additional glycol component and an additional diacid component are further added thereto to carry out an esterification reaction (S310). A molten polyester resin is obtained through a polycondensation reaction of the esterification product thus obtained, and by-products formed during the reaction are discharged (S500). Thereafter, a further solid-state polymerization is carried out, if necessary, followed by processing to finally obtain a polyester resin (S400).

Hereinafter, each step will be described in detail.

Recycled Bis(2-hydroxyethyl) Terephthalate

Bis(2-hydroxyethyl) terephthalate is an ester of two ethylene glycols and one terephthalic acid. For example, it is a compound formed as an intermediate in the process of preparing polyester such as polyethylene terephthalate (PET) through the polymerization of ethylene glycol and terephthalic acid or its ester.

Bis(2-hydroxyethyl) terephthalate (BHET), which is used as a polymerization raw material for the polyester resin according to the present invention, is obtained from waste polyester having a repeat unit of ethylene glycol and terephthalic acid like polyethylene terephthalate (PET) or glycol-modified polyethylene terephthalate (PETG). For example, it may be obtained by well-known depolymerization methods such as glycolysis, hydrolysis, and methanolysis.

In the present specification, bis(2-hydroxyethyl) terephthalate (BHET) obtained by the depolymerization of waste polyester as described above is referred to as "recycled bis(2-hydroxyethyl) terephthalate (recycled BHET)," or abbreviated as r-BHET or rBHET, which needs to be understood as distinct from a pure BHET compound.

Specifically, recycled BHET may contain reagents or solvents used in various chemical steps during the depolymerization of waste polyester, or by-products formed by side reactions with them. These impurities may remain in trace amounts even after several rounds of purification. Thus, recycled BHET generally contains trace amounts of organic and inorganic impurities in addition to BHET as the main component. For this reason, recycled BHET can also be viewed as a kind of composition comprising two or more components, i.e., a BHET composition. It may be used as a polymerization raw material for producing a polyester resin.

Specifically, recycled BHET may comprise trace amounts of a different type of an organic component, such as BHET analogs such as mono(2-hydroxyethyl) terephthalic acid (MHET), by-products such as BHET dimers, BHET trimers, and diethylene glycol esters, metal ions as inorganic components, and residual solvent components, in addition to BHET as the main component.

In the present invention, recycled BHET in which the content of such heterogeneous organic components is adjusted to a certain range is used. The content of each component in recycled BHET can be derived by measuring the fraction (%) of a peak area out of the total peak area in a spectrum obtained using high-performance liquid chromatography (HPLC).

Specifically, the recycled bis(2-hydroxyethyl) terephthalate (BHET) as a raw material in the present invention has a peak area fraction of BHET of 96% or more when measured by high-performance liquid chromatography (HPLC). More specifically, the peak area fraction of BHET measured by HPLC may be 96.5% or more, 97% or more, 97.5% or more, or 98% or more.

In addition, the recycled bis(2-hydroxyethyl) terephthalate may have a peak area fraction of organic impurities measured by HPLC of less than 5% in total, specifically, less than 4%, less than 3%, less than 2%, less than 1%, or less than 0.7%.

In particular, the polyester resin according to the present invention comprises recycled BHET in which the content of diethylene glycol esters (DEG esters) is adjusted to a certain level or less. For example, the recycled bis(2-hydroxyethyl) terephthalate may have a peak area fraction of diethylene glycol ester compounds of less than 2% in total when measured by HPLC. Specifically, the peak area fraction of diethylene glycol ester compounds may be less than 1.5%, less than 1%, less than 0.8%, or less than 0.7%, in total.

As an example, the diethylene glycol ester compounds may be a condensate between an aromatic dicarboxylic acid such as terephthalic acid and diethylene glycol. As another example, the diethylene glycol ester compounds may be a condensate between an aromatic dicarboxylic acid such as terephthalic acid and a glycol (e.g., ethylene glycol) in addition to diethylene glycol.

According to an embodiment, the recycled BHET may comprise 2-hydroxyethyl[2-(2-hydroxyethoxy)ethyl] terephthalate (CAS No. 65133-69-9) of the following Formula 1 as a first diethylene glycol ester. According to another embodiment, the recycled BHET may comprise bis[2-(2-hydroxyethoxy)ethyl]benzene-1,4-dicarboxylate (CAS No. 26850-76-0) of the following Formula 2 as a second diethylene glycol ester. If a polyester resin is prepared from recycled BHET in which the contents of the first diethylene glycol ester and the second diethylene glycol ester are adjusted to a certain level or less, even though it is a polyester resin regenerated through chemical recycling, it is hardly deteriorated in quality as compared with a virgin resin.

[Formula 1]

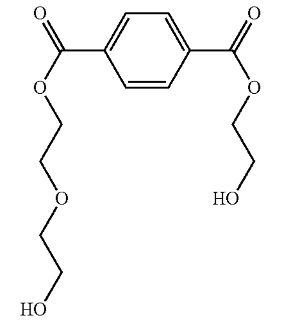

[Formula 2]

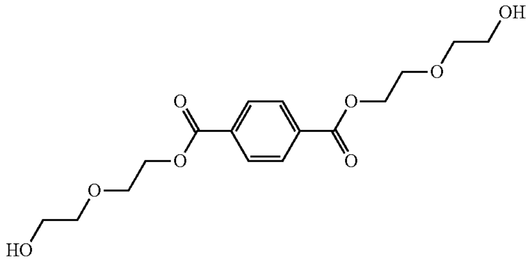

According to an embodiment, the recycled bis(2-hydroxyethyl) terephthalate (BHET) has a peak area fraction of 2-hydroxyethyl[2-(2-hydroxyethoxy)ethyl] terephthalate (first diethylene glycol ester) of 2.5% or less when measured by high-performance liquid chromatography (HPLC). Specifically, the peak area fraction of 2-hydroxyethyl[2-(2-hydroxyethoxy)ethyl] terephthalate measured by HPLC may be 2.0% or less, 1.5% or less, 1.0% or less, or 0.5% or less.

According to another embodiment, the recycled bis(2-hydroxyethyl) terephthalate (BHET) has a peak area fraction of bis[2-(2-hydroxyethoxy)ethyl]benzene-1,4-dicarboxylate (second diethylene glycol ester) of 0.5% or less when measured by high-performance liquid chromatography (HPLC). Specifically, the peak area fraction of bis[2-(2-hydroxyethoxy)ethyl]benzene-1,4-dicarboxylate measured by HPLC may be 0.2% or less, more specifically, 1.5% or less, 1.0% or less, or 0.5% or less.

In addition, the recycled bis(2-hydroxyethyl) terephthalate may have a peak area fraction of oligomers of 3% or less in total when measured by HPLC.

Specifically, the recycled bis(2-hydroxyethyl) terephthalate may have a peak area fraction of BHET dimers of less than 3%, less than 2%, less than 1%, or less than 0.7%, when measured by HPLC. In addition, the bis(2-hydroxyethyl) terephthalate produced by the above process may have a peak area fraction of BHET trimers measured by HPLC of less than 1%, less than 0.5%, less than 0.3%, less than 0.1%, or 0%.

In addition, the recycled bis(2-hydroxyethyl) terephthalate may further comprise impurities having a structure similar to that of bis(2-hydroxyethyl) terephthalate. For example, it may comprise at least one selected from the group consisting of monohydroxyethyl terephthalic acid (MHET), bis(2-hydroxypropyl) terephthalate, and monohydroxyethylethoxy terephthalic acid. The impurities having a structure similar to that of bis(2-hydroxyethyl) terephthalate may have a peak area fraction of less than 3%, less than 2%, less than 1%, or less than 0.5%, when measured by HPLC.

In addition, the total content of residual solvents (e.g., ethylene glycol) in the recycled bis(2-hydroxyethyl) terephthalate may be less than 1% by weight when calculated based on a weight ratio detected by gas chromatography analysis. Specifically, the total content of residual solvents may be less than 0.5% by weight, less than 0.3% by weight, less than 0.2% by weight, less than 0.1% by weight, or less than 0.9% by weight.

In addition, the recycled bis(2-hydroxyethyl) terephthalate may have a yellow index (YID) of 3.0 or less as measured with a spectrophotometer in a solution of 25% by weight. Specifically, the yellow index may be 2.5 or less, 2.0 or less, 1.5 or less, or 1.0 or less.

In addition, the recycled bis(2-hydroxyethyl) terephthalate may have a total content of inorganic substances of less than 5 ppm as measured by inductively coupled plasma atomic emission spectroscopy (ICP-AES). Specifically, the total content of inorganic substances may be less than 3 ppm, less than 1 ppm, or nearly 0 ppm.

Preparation of Recycled Bis(2-hydroxyethyl) Terephthalate

Although bis(2-hydroxyethyl) terephthalate used in the preparation of a polyester resin according to the present invention is a recycled monomer obtained by the depolymerization of waste polyester, it has high purity and a low content of impurities such as diethylene glycol esters.

Such bis(2-hydroxyethyl) terephthalate can be obtained by carrying out a depolymerization reaction in multiple stages, while significantly lowering the temperature of the latter stage, followed by ion exchange and distillation of an unreacted glycol after the depolymerization reaction.

The process for preparing recycled bis(2-hydroxyethyl) terephthalate according to an embodiment may comprise (1a) subjecting waste polyester to depolymerization by a first glycolysis reaction at a temperature of 180° C. to 200° C. to obtain a first reactant; (1b) subjecting the first reactant to depolymerization by a second glycolysis reaction at a temperature of 150° C. to 170° C. to obtain a second reactant; (1c) subjecting the second reactant to ion exchanging through an ion-exchange resin to obtain a third reactant; (1d) removing an unreacted glycol from the third reactant through distillation at a temperature of 150° C. or lower to obtain a fourth reactant; and (1e) subjecting the fourth reactant to distillation to obtain crude bis(2-hydroxyethyl) terephthalate.

According to the above process, bis(2-hydroxyethyl) terephthalate (BHET) can be produced with high purity by carrying out a depolymerization reaction in multiple stages, while significantly lowering the temperature of the latter stage, thereby reducing the formation of diethylene glycol and impurities derived therefrom. In addition, according to the above process, it is possible to prepare bis(2-hydroxyethyl) terephthalate with enhanced quality in terms of color by further carrying out ion exchange and distillation of an unreacted glycol after the depolymerization reaction, thereby reducing the formation of oligomers and removing chromophores.

According to another embodiment, prior to step (1a), a step of pulverizing the waste polyester to a size of a certain level or below may be further carried out. The waste polyester may have a particulate or fibrous form with a particle diameter of 4 mm or less. If the depolymerization is carried out as the particle diameter or diameter of waste polyester is adjusted within the specific range, solvation can be expedited even under the conditions of relatively low temperatures and short reaction time.

According to another embodiment, the first glycolysis reaction in step (1a) is carried out in the presence of a catalyst. The catalyst comprises a metal acetate or an anhydride or a hydride thereof. More specifically, it may be at least one selected from the group consisting of zinc acetate, sodium acetate, cobalt acetate, and manganese acetate, or in the form of a hydrate or anhydride thereof. In addition, the catalyst may be used in an amount of 0.2 part by weight to 0.4 part by weight relative to 100 parts by weight of the waste polyester.

According to another embodiment, a step of cooling the second reactant obtained in step (1b) to a certain temperature or lower may be further carried out.

According to another embodiment, prior to the ion exchange in step (1c), a step of removing insoluble foreign substances from the second reactant through filtration may be further carried out. Specifically, a step of cooling the second reactant to 120° C. or lower and filtering it upon the addition of a filter aid may be further carried out.

According to another embodiment, prior to the ion exchange in step (1c), a step of removing insoluble foreign substances from the second reactant through filtration may be further carried out.

According to another embodiment, the ion-exchange resin in step (1c) is used in an amount of 1 part by weight to 20 parts by weight relative to 100 parts by weight of the waste polyester and comprises at least one selected from the group consisting of a strongly acidic cation-exchange resin, a weakly acidic cation-exchange resin, and a chelate resin.

According to another embodiment, the distillation to remove an unreacted glycol in step (1d) may be carried out at a temperature of 100° C. to 130° C.

According to another embodiment, the distillation to obtain crude bis(2-hydroxyethyl) terephthalate in step (1e) may be carried out by thin film evaporation under a pressure of 0.05 Torr to 0.4 Torr.

According to another embodiment, the process may further comprise, after the distillation in step (1e), adsorbing-crystallizing the crude bis(2-hydroxyethyl) terephthalate. The adsorption-crystallization may be carried out by adding an adsorbent using water as a solvent, filtering, and crystallization.

According to a specific embodiment, first, waste polyester is pulverized to a size of 4 mm or less to be prepared, ethylene glycol is added thereto, which is then subjected to a first glycolysis reaction at a temperature of 180° C. to 200° C. in the presence of a zinc acetate catalyst for about 2 hours, and ethylene glycol is further added thereto, which is then subjected to a second glycolysis reaction at a temperature of 150° C. to 170° C. for about 2 hours. Thereafter, it is cooled to 120° C. or lower using a reduced pressure flash, a small amount of a filter aid is added thereto, which is then filtered to separate insoluble foreign substances through solid-liquid separation, and it is passed through a column filled with an ion-exchange resin to carry out ion exchange. Then, an unreacted glycol is recovered at a temperature of 100° C. to 130° C., purification is carried out by thin film distillation at 190° C. to 250° C., and, finally, an adsorption-crystallization step is carried out to obtain bis(2-hydroxyethyl) terephthalate with high purity and high quality.

According to the above process, a two-stage glycolysis reaction (i.e., a first glycolysis reaction and a second glycolysis reaction) is carried out. If the solvation is expedited in the first glycolysis reaction, the transesterification reaction of the waste polyester can be performed under the conditions of lower temperatures and short reaction time in the second glycolysis reaction. Thus, it is possible to significantly reduce the concentration of diethylene glycol (DEG) naturally formed at a common glycolysis reaction temperature and to significantly reduce the content of diethylene glycol esters in bis(2-hydroxyethyl) terephthalate finally prepared.

Preparation of an Aqueous Solution of Recycled Bis(2-hydroxyethyl) Terephthalate Recycled bis(2-hydroxyethyl) terephthalate prepared as described above may be thereafter stored for a period of time before being put into the polymerization of a polyester resin.

The quality of recycled BHET may deteriorate depending on the storage conditions during this period, in which case the quality of a final polyester resin may be affected.

According to the present invention, when recycled bis(2-hydroxyethyl) terephthalate is mixed with water to prepare an aqueous solution under specific temperature and concentration conditions, storage stability can be secured, and the uniformity of a raw material and the reaction efficiency can be enhanced by introducing the aqueous solution of recycled BHET into the polymerization for a polyester resin.

The temperature (dissolution temperature) for preparing an aqueous solution of recycled BHET of the present invention is 60° C. to 110° C., in which range the purity and color of recycled BHET can be maintained to be excellent. For example, the temperature for preparing an aqueous solution of recycled BHET may be 60° C. or higher, 70° C. or higher, 75° C. or higher, or 85° C. or higher, and may be 110° C. or lower, 100° C. or lower, 95° C. or lower, or 90° C. or lower.

In addition, the temperature for storing the aqueous solution of recycled BHET may be the same as the temperature (dissolution temperature) for preparing the aqueous solution of recycled BHET. That is, an aqueous solution of recycled BHET may be prepared at a temperature of 60° C. to 110° C. and may be stored while the temperature condition is maintained.

The concentration of the aqueous solution of recycled BHET of the present invention is 50% by weight to 95% by weight, in which range the change in temperature is small by virtue of the high specific heat of water as a solvent, whereby the storage stability is excellent, and the amount of heat required to evaporate water from the aqueous solution can be reduced. For example, the concentration of the aqueous solution of recycled BHET may be 50% by weight or more, 55% by weight or more, 65% by weight or more, or 75% by weight or more, and may be 95% by weight or less, 90% by weight or less, 85% by weight or less, or 80% by weight or less.

As a specific example, the process for preparing an aqueous solution of recycled BHET comprises (2a) mixing the recycled bis(2-hydroxyethyl) terephthalate with water at 60° C. to 110° C.; and (2b) adjusting the concentration to 50% by weight to 95% by weight through further addition or evaporation of water after the mixing.

The storage stability of the aqueous solution of recycled BHET can be evaluated by measuring the purity and yellow index of the aqueous solution of recycled BHET after storage for a certain period of time at the preparation temperature (i.e., 60 to 110° C.) of the aqueous solution of recycled BHET.

According to the present invention, as recycled BHET is prepared and stored as an aqueous solution under specific temperature and concentration conditions, the decrease in purity and color is very small even after storage for a certain period of time.

For example, when the aqueous solution of recycled BHET is stored at 60° C. to 110° C. for 5 days, the purity of the recycled BHET may be measured to have a difference of 5% or less from the initial purity. Such a difference in purity may be confirmed by comparing the peak area fraction (%) of BHET obtained by analyzing the recycled BHET by high-performance liquid chromatography (HPLC). Specifically, when recycled BHET obtained by storing the aqueous solution of recycled BHET at 60° C. to 110° C. for 5 days and then evaporating water is measured by high-performance liquid phase chromatography (HPLC), the peak area fraction of BHET may be 90% or more, 93% or more, or 95% or more.

In addition, when recycled bis(2-hydroxyethyl) terephthalate obtained by storing the aqueous solution of recycled bis(2-hydroxyethyl) terephthalate at 60° C. to 110° C. for 5 days and then evaporating water is dissolved in ethylene glycol at a concentration of 25% by weight at 120° C. for 1 hour, the yellow index (YID) may be measured to be 5 or less. For example, the yellow index (YID) after storage for 5 days may be 5 or less, 4.5 or less, 4 or less, 3.5 or less, 3 or less, or 2.5 or less.

In addition, the yellow index (YID) after storage for 5 days may have a difference within 6, within 4, or within 2, as compared with the initial value. Here, the initial yellow index is obtained by measuring in the same way (that is, dissolved in ethylene glycol at a concentration of 25% by weight at 120° C. for 1 hour for measurement) for recycled BHET obtained by the depolymerization (i.e., recycled BHET prior to mixing with water to make an aqueous solution).

Process for Preparing a Polyester Resin

The aqueous solution of recycled bis(2-hydroxyethyl) terephthalate may be used to polymerize a polyester resin.

As an example, the aqueous solution of recycled bis(2-hydroxyethyl) terephthalate, as it is, may be introduced into a polymerization reaction for a polyester, which may be advantageous in terms of uniform supply of a raw material and reaction efficiency. In particular, when it is introduced into a polymerization reaction as an aqueous solution, it is possible to continuously introduce the recycled BHET, thereby enabling a continuous process of a uniform polymerization reaction.

As another example, the water in the aqueous solution of recycled bis(2-hydroxyethyl) terephthalate may be evaporated to obtain solid-phase recycled bis(2-hydroxyethyl) terephthalate, which may then be introduced into the polymerization reaction for a polyester resin. In such a case, there is an advantage in that the existing process and equipment for introducing solid-phase recycled BHET can be used as it is by storing it as an aqueous solution for thermal stability and then evaporating water and introducing it into the polymerization reaction.

In the polymerization, an esterification reaction (first polymerization reaction step) and a polycondensation reaction (second polymerization reaction step) may be sequentially carried out.

The polyester resin according to the present invention may be prepared by further adding terephthalic acid or a derivative thereof and/or ethylene glycol in addition to the recycled bis(2-hydroxyethyl) terephthalate. In addition, the polyester resin may be prepared as a copolymer by further adding comonomers of other diacids and/or glycols.

For example, at least one monomer selected from the group consisting of (a) a dicarboxylic acid or a derivative thereof, (b) ethylene glycol or diethylene glycol, and (c) a diol-based comonomer may be further introduced into the esterification reaction.

The dicarboxylic acid may comprise at least one selected from terephthalic acid and isophthalic acid. In addition, the diol-based comonomer may comprise at least one selected from the group consisting of cyclohexanedimethanol, cyclohexanedimethanol derivatives, and isosorbide. The cyclohexanedimethanol derivative may be 4-(hydroxymethyl)cyclohexylmethyl-4-(hydroxymethyl)cyclohexanecarboxylate or 4-(4-(hydroxymethyl)cyclohexylmethoxymethyl)cyclohexylmethanol.

The diol-based comonomer may further comprise 1,2-propanediol, 1,3-propanediol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 1,4-butanediol, 2,3-butanediol, 3-methyl-1,5-pentanediol, 3-methyl-2,4-pentanediol, 1,6-hexanediol, 1,2-cyclohexanediol, and 1,4-cyclohexanediol.

The esterification reaction may be carried out in the presence of an esterification reaction catalyst. For example, a zinc-based compound may be used. Specific examples of the zinc-based catalyst include zinc acetate, zinc acetate hydrate, zinc chloride, zinc sulfate, zinc sulfide, zinc carbonate, zinc citrate, zinc gluconate, or mixtures thereof.

The esterification reaction may be carried out, for example, at a pressure of 0 $kgf/cm^2$ to 10.0 $kgf/cm^2$ and a temperature of 150° C. to 300° C. The esterification reaction conditions may be appropriately adjusted according to the specific characteristics of the polyester to be produced, the ratio of each component, or process conditions. Specifically, the pressure in the esterification reaction may be 0 $kg/cm^2$ to 5.0 $kg/cm^2$, more specifically, 0.1 $kg/cm^2$ to 3.0 $kg/cm^2$. In addition, the temperature in the esterification reaction may be 200° C. to 270° C., more specifically, 240° C. to 260° C.

The esterification reaction may be carried out in a batch or continuous type. Although each of the raw materials may be separately fed, it is preferable to feed them in the form of a slurry in which a diol component, a dicarboxylic acid component, and recycled BHET are mixed. In addition, a diol component such as isosorbide, which is solid at room temperature, may be dissolved in water or ethylene glycol and then mixed with a dicarboxylic acid component such as terephthalic acid to prepare a slurry. Alternatively, isosorbide may be melted at 60° C. or higher, which is then mixed with a dicarboxylic acid component such as terephthalic acid and other diol components to prepare a slurry. In addition, water may be additionally added to the mixed slurry to help increase the fluidity of the slurry. In addition, in a continuous type, liquid raw materials (e.g., aqueous solution of recycled BHET) may be continuously fed to a reactor using a pump or the like. The hourly feeding amount of raw materials can be determined by dividing the total amount of raw materials to be fed by time to achieve the target production per day (e.g., 50 t/day).

The mixture of the aqueous solution of recycled bis(2-hydroxyethyl) terephthalate and other additive components is left in the esterification reactor for a certain period of time, for example, 1 hour to 24 hours or 4 hours to 10 hours, which is then transferred to a polycondensation reactor. The polycondensation reaction may produce a relatively low molecular weight polyester resin through melt polymerization. In addition, a polyester resin having a relatively high molecular weight may be produced through solid-state polymerization after the melt polymerization.

The temperature in the polycondensation reaction may be 150° C. to 300° C., specifically, 200° C. to 290° C., more specifically, 260° C. to 280° C. In addition, the pressure in the polycondensation reaction may be 0.01 mmHg to 600 mmHg, specifically, 0.05 mmHg to 200 mmHg, more specifically, 0.1 mmHg to 100 mmHg. As the reduced pressure condition is adopted in the polycondensation reaction, glycol, which is a by-product of the polycondensation reaction, can be removed from the system. If the pressure in the polycondensation reaction exceeds the range of 0.01 mmHg to 400 mmHg, the removal of by-products may be insufficient. In addition, if the temperature in the polycondensation reaction is lower than 150° C., a glycol as a by-product of the reaction cannot be effectively removed from the system; thus, the intrinsic viscosity of a final reaction product is low, resulting in a decrease in the physical properties of the final polyester resin. If the temperature in the polycondensation reaction exceeds 300° C., the possibility of yellowing of a final polyester resin increases. In addition, the polycondensation reaction may be carried out for a necessary period of time, for example, an average residence time of 1 hour to 24 hours, until the intrinsic viscosity of a final reaction product reaches an appropriate level.

In addition, the polycondensation reaction may be carried out in the presence of a polycondensation catalyst. The polycondensation catalyst may be, for example, a titanium-based compound, a germanium-based compound, an antimony-based compound, an aluminum-based compound, a tin-based compound, or a mixture thereof. Examples of the titanium compound include tetraethyl titanate, acetyltripropyl titanate, tetrapropyl titanate, tetrabutyl titanate, 2-ethylhexyl titanate, octylene glycol titanate, lactate titanate, triethanolamine titanate, acetylacetonate titanate, ethylacetoacetic ester titanate, isostearyl titanate, titanium dioxide, and the like. Examples of the germanium-based compound include germanium dioxide, germanium tetrachloride, germanium ethylene glycol oxide, germanium acetate, or mixtures thereof. Preferably, germanium dioxide can be used. Both crystalline and amorphous germanium dioxide may be used, and glycol-soluble ones may also be used. The amount of the polycondensation catalyst used may be such that the amount of titanium element relative to the weight of the polyester resin is about 1 to 100 ppm, more preferably, about 1 to 50 ppm.

In addition to the polycondensation catalyst, a stabilizer, a colorant, a crystallizing agent, an antioxidant, a branching agent, or the like may be further used. The timing of adding these additives is not particularly limited, and they may be added at any time during the preparation step of the polyester resin.

As the stabilizer, phosphorus-based compounds such as phosphoric acid, trimethyl phosphate, triethyl phosphate, and triethyl phosphonoacetate may be generally used. The amount thereof added may be such that 10 to 200 ppm relative to the weight of the polyester resin based on the amount of elements. In addition, common colorants such as cobalt acetate and cobalt propionate may be exemplified as the colorant added to enhance the color of the polyester resin. The amount thereof added may be such that 10 to 200 ppm relative to the weight of the polyester resin based on the amount of cobalt element. If necessary, anthraquinone-based compounds, perinone-based compounds, azo-based compounds, methine-based compounds, or the like may be used as an organic colorant. Commercially available toners such as Polysynthren Blue RLS from Clarient or Solvaperm Red BB from Clarient may be used. The amount of the organic compound colorant added may be adjusted to 0 to 50 ppm based on the weight of the polyester resin. A crystal nucleating agent, an ultraviolet absorber, a polyolefin resin, a polyamide resin, and the like may be exemplified as the crystallizing agent. Hindered phenol-based antioxidants, phosphite-based antioxidants, thioether-based antioxidants, or mixtures thereof may be exemplified as the antioxidant. Conventional branching agents having three or more functional groups, for example, trimellitic anhydride, trimethylol propane, trimellitic acid, or mixtures thereof may be exemplified as the branching agent.

Composition and Characteristics of the Polyester Resin

The polyester resin of the present invention is a polyester resin regenerated through the chemical recycling of waste polyester.

Specifically, since the polyester resin of the present invention is polymerized using recycled BHET, it comprises a repeat unit derived from recycled BHET in the polymer chain.

The content of recycled BHET in the polyester resin of the present invention may be 1% by weight or more, 5% by weight or more, 10% by weight or more, 30% by weight or more, 50% by weight or more, 70% by weight or more, or 90% by weight or more. In addition, the content of recycled BHET may be 100% by weight or less, 99% by weight or less, 80% by weight or less, 60% by weight or less, 40% by weight or less, or 20% by weight or less.

As an example, the recycled bis(2-hydroxyethyl) terephthalate may be employed in an amount of 10% by weight to 99% by weight based on the weight of the polyester resin.

Meanwhile, since bis(2-hydroxyethyl) terephthalate has a structure in which two ethylene glycols and one terephthalic acid are bonded, the polyester resin of the present invention may essentially comprise a repeat unit derived from ethylene glycol and terephthalic acid.

As described above, the polyester resin of the present invention comprises a diacid component and a glycol component as monomers constituting the same. In addition, the polyester resin of the present invention may further comprise an additional diacid component and an additional glycol component for the polymerization of polyester.

In the polyester resin of the present invention, the diacid component may be a dicarboxylic acid or a derivative thereof, and the glycol component may be a diol.

In particular, the dicarboxylic acid comprises terephthalic acid, and the physical properties such as thermal resistance, chemical resistance, and weather resistance of a polyester resin can be enhanced by terephthalic acid. For example, terephthalic acid may be employed in an amount of 5% by mole to 100% by mole based on the number of moles of the entire dicarboxylic acid. In addition, the terephthalic acid component may be formed from a terephthalic acid alkyl ester such as dimethyl terephthalic acid.

In addition, the diol comprises ethylene glycol or diethylene glycol, and ethylene glycol or diethylene glycol may contribute to enhancing the transparency and impact resistance of a polyester resin. For example, ethylene glycol and/or diethylene glycol may be employed in an amount of 5% by mole to 100% by mole based on the number of moles of the entire diol.

According to an embodiment, the polyester resin of the present invention may be a copolymerized resin comprising two or more dicarboxylic acid components and/or two or more diol components.

Specifically, the dicarboxylic acid component may further comprise an aromatic dicarboxylic acid component, an aliphatic dicarboxylic acid component, or a mixture thereof, other than terephthalic acid. The dicarboxylic acid other than terephthalic acid may be employed in an amount of 1% by mole to 30% by mole based on the weight of the entire dicarboxylic acid components.

The aromatic dicarboxylic acid component may be an aromatic dicarboxylic acid having 8 to 20 carbon atoms, preferably, 8 to 14 carbon atoms, or a mixture thereof. Examples of the aromatic dicarboxylic acid include isophthalic acid, naphthalenedicarboxylic acids such as 2,6-naphthalenedicarboxylic acid, diphenyl dicarboxylic acid, 4,4'-stilbendicarboxylic acid, 2,5-furandicarboxylic acid, 2,5-thiophenedicarboxylic acid, and the like, but it is not limited thereto.

The aliphatic dicarboxylic acid component may be an aliphatic dicarboxylic acid having 4 to 20 carbon atoms, preferably, 4 to 12 carbon atoms, or a mixture thereof. Examples of the aliphatic dicarboxylic acid include linear, branched, or cyclic aliphatic dicarboxylic acid components such as cyclohexanedicarboxylic acids such as 1,4-cyclohexanedicarboxylic acid and 1,3-cyclohexanedicarboxylic acid, phthalic acid, sebacic acid, succinic acid, isodecylsuccinic acid, maleic acid, fumaric acid, adipic acid, glutaric acid, azelaic acid, and the like, but it is not limited thereto.

In addition, the diol component may further comprise a comonomer other than ethylene glycol or diethylene glycol. The comonomer may comprise, for example, at least one selected from the group consisting of cyclohexanedimethanol, cyclohexanedimethanol derivatives, and isosorbide.

The cyclohexanedimethanol (e.g., 1,2-cyclohexanedimethanol, 1,3-cyclohexanedimethanol, and 1,4-cyclohexanedimethanol) may contribute to enhancing the transparency and impact resistance of a polyester resin produced. For example, cyclohexanedimethanol may be employed in an amount of 5% by mole to 90% by mole based on the number of moles of the entire diol. The cyclohexanedimethanol derivative may be 4-(hydroxymethyl)cyclohexylmethyl-4-(hydroxymethyl)cyclohexanecarboxylate or 4-(4-(hydroxymethyl)cyclohexylmethoxymethyl)cyclohexylmethanol. The cyclohexanedimethanol derivatives may be employed in an amount of 0.1% by mole to 25% by mole based on the number of moles of the entire diol.

Isosorbide may enhance the processability of the final polyester resin. Although the transparency and impact resistance of a polyester resin are enhanced by the diol component of cyclohexanedimethanol and ethylene glycol, shear fluidization characteristics should be improved and the crystallization rate should be delayed for processability; however, it is difficult to achieve this effect with cyclohexanedimethanol and ethylene glycol alone. Thus, if isosorbide is employed as a diol component, the shear fluidization characteristics are improved and the crystallization rate is delayed while transparency and impact resistance are maintained, whereby it is possible to improve the processability of a polyester resin produced. Preferably, isosorbide may be employed in an amount of 0.1% by mole to 50% by mole based on the number of moles of the entire diol.

As a specific example, the polyester resin comprises a diacid component and a glycol component, wherein the diacid component may comprise at least one selected from the group consisting of terephthalic acid, isophthalic acid, dimethyl isophthalate, phthalic acid, dimethyl phthalate, phthalic anhydride, 2,6-naphthalenedicarboxylic acid, dimethyl 2,6-naphthalenedicarboxylate, diphenyl dicarboxylic acid, 1,4-cyclohexanedicarboxylic acid, 1,3-cyclohexanedicarboxylic acid, dimethyl 1,4-cyclohexanedicarboxylate, dimethyl 1,3-cyclohexanedicarboxylate, sebacic acid, succinic acid, isodecylsuccinic acid, maleic acid, maleic anhydride, fumaric acid, adipic acid, glutaric acid, and azelaic acid, and the glycol component may comprise at least one selected from the group consisting of isosorbide (ISB), ethylene glycol, 1,2-propanediol, 1,3-propanediol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 1,4-butanediol, 2,3-butanediol, 3-methyl-1,5-pentanediol, 3-methyl-2,4-pentanediol, 1,6-hexanediol, 1,2-cyclohexanediol, 1,4-cyclohexanediol, diethylene glycol, 4-(hydroxymethyl)cyclohexylmethyl-4-(hydroxymethyl)cyclohexanecarboxylate, and 4-(4-(hydroxymethyl)cyclohexylmethoxymethyl)cyclohexylmethanol.

According to an embodiment, the polyester resin may further comprise at least one monomer selected from the group consisting of (a) a dicarboxylic acid or a derivative thereof, (b) ethylene glycol or diethylene glycol, and (c) a diol-based comonomer in addition to bis(2-hydroxyethyl) terephthalate. The dicarboxylic acid may comprise at least one selected from terephthalic acid and isophthalic acid. In addition, the diol-based comonomer may comprise at least one selected from the group consisting of cyclohexanedimethanol, cyclohexanedimethanol derivatives, and isosorbide. The cyclohexanedimethanol derivative may be 4-(hydroxymethyl)cyclohexylmethyl-4-(hydroxymethyl) cyclohexanecarboxylate or 4-(4-(hydroxymethyl) cyclohexylmethoxymethyl)cyclohexylmethanol. The diol-based comonomer may further comprise 1,2-propanediol, 1,3-propanediol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 1,4-butanediol, 2,3-butanediol, 3-methyl-1,5-pentanediol, 3-methyl-2,4-pentanediol, 1,6-hexanediol, 1,2-cyclohexanediol, and 1,4-cyclohexanediol.

The polyester resin may have a value obtained by subtracting the b value from the L value of 85 or more when Hunter Lab color space is measured. For example, the L−b value may be 85 or more, 86 or more, 87 or more, 88 or more, 89 or more, 90 or more, or 91 or more. In addition, the upper limit of the L−b value is not particularly limited. But it may be, for example, 100 or less, 99 or less, 98 or less, 97 or less, or 95 or less. The measurement of the Hunter Lab color space may be carried out by making a specimen having a thickness of 6 mm with the polyester resin.

The intrinsic viscosity of the polyester resin according to the present invention at 35° C. may be 0.5 dl/g or more, 0.6 dl/g or more, or 0.7 dl/g or more, and may be 1.2 dl/g or less, 1.1 dl/g or less, 1.0 dl/g or less, or 0.9 dl/g or less. For example, the polyester resin may have an intrinsic viscosity of 0.5 dl/g to 1.2 dl/g at 35° C. Specifically, the polyester resin may have an intrinsic viscosity of 0.5 dl/g to 0.9 dl/g at 35° C.

The polyester resin according to the present invention can be used as a material for beverage-filling containers, packaging films, audio and video films, and the like by virtue of its excellent color, mechanical strength, thermal resistance, transparency, and gas barrier properties. In addition, polyester sheets or plates prepared from the polyester resin according to the present invention have good transparency and excellent mechanical strength, so that they can be used as raw materials for cases, boxes, partitions, shelves, panels, packaging materials, building materials, interior and exterior materials, and the like. In addition, the polyester resin according to the present invention can be used as an industrial material such as medical fibers and tire cords.

Accordingly, the present invention provides an article, which comprises the polyester resin.

MODE FOR THE INVENTION

Hereinafter, the present invention will be described in more detail with reference to embodiments. However, these examples are provided only for illustration purposes, and the present invention is not limited thereto.

Preparation and Evaluation of Recycled Bis(2-hydroxyethyl) Terephthalate

Preparation Example: r-BHET_A1 (Recycled BHET)

A first reactor made of stainless steel (SUS) was charged with 1,000 g of a waste polyester resin pulverized to a particle size of 4 mm or less, 2,000 g of ethylene glycol (EG), and 3.5 g of zinc acetate anhydride. The temperature inside the reactor was raised to 180° C., and depolymerization (first glycolysis reaction) was carried out for 2 hours. The reactant (first reactant) thus obtained was transferred to a second reactor and cooled to 150° C. 2,000 g of ethylene glycol was further added thereto, and depolymerization (second glycolysis reaction) was carried out for 2 hours while the reactor temperature was maintained at 150° C. The reactant (second reactant) thus obtained was cooled to 120° C. through reduced pressure flash, and 16 g of a filter aid was added thereto, followed by pressurized filtration to carry out solid-liquid separation. The separated liquid reactant was passed through a column filled with an ion-exchange resin (BC107(H) of Bonlite) to remove ionic impurities to obtain a mixture (third reactant) containing bis(2-hydroxyethyl) terephthalate and ethylene glycol. The mixture (third reactant) was transferred to a 10-liter distillation apparatus, and vacuum distillation was carried out at 130° C. to recover unreacted ethylene glycol. The reactant (fourth reactant) from which ethylene glycol had been removed was subjected to thin film evaporation at 220° C. and 0.08 Torr in a thin film evaporator (VKL70-4S of VTA) to obtain 1,040 g of a product from which dimers or higher oligomers had been removed. Thereafter, for adsorption-crystallization, 1,040 g of the above product and 3,120 g of distilled water were charged to a 20-liter glass reactor, dissolved at a temperature of 70° C., and then 5.2 g of activated carbon was added thereto, followed by stirring for 30 minutes and filtration thereof. The filtrate was cooled to room temperature for the crystallization thereof, filtered, and dried in a vacuum oven. As a result, 990 g of a final product containing bis(2-hydroxyethyl) terephthalate was obtained.

Preparation Example: r-BHET_A2 (Recycled BHET)

980 g of a final product containing bis(2-hydroxyethyl) terephthalate (referred to as r-BHET_A2) was obtained through the same procedure as in the Preparation Example of r-BHET_A1, except that the first glycolysis reaction was carried out at 180° C. for 1 hour.

Preparation Example: r-BHET_A3 (Recycled BHET)

985 g of a final product containing bis(2-hydroxyethyl) terephthalate (referred to as r-BHET_A3) was obtained through the same procedure as in the Preparation Example of r-BHET_A1, except that 1,000 g of a waste fiber was used as a raw material for waste polyester.

Preparation Example: r-BHET_A5 (Recycled BHET)

1,050 g of a final product containing bis(2-hydroxyethyl) terephthalate (referred to as r-BHET_A5) was obtained through the same procedure as in the Preparation Example of r-BHET_A1, except that no adsorption-crystallization step was carried out after the thin film evaporation.

Preparation Example: r-BHET_B2 (Recycled BHET)

A reactor made of stainless steel (SUS) was charged with 1,000 g of a waste polyester resin having a particle size of 4 mm or less, 4,000 g of ethylene glycol (EG), and 3.5 g of zinc acetate anhydride. The temperature inside the reactor was raised to 210° C., and depolymerization (glycolysis reaction) was carried out for 4 hours. The reactant thus obtained was cooled to 30° C., and crystallization of bis(2-hydroxyethyl) terephthalate was carried out for 2 hours. The slurry of bis(2-hydroxyethyl) terephthalate and ethylene glycol thus obtained was subjected to solid-liquid separation in a centrifugal separator. Bis(2-hydroxyethyl) terephthalate obtained through centrifugation was washed twice with a sufficient amount of distilled water, and the residual solvent was removed in an oven to obtain about 1,010 g of a final product containing bis(2-hydroxyethyl) terephthalate (referred to as r-BHET_B2).

Test Example 1: Analysis of r-BHET Components-HPLC

The components of recycled bis(2-hydroxyethyl) terephthalate (BHET) were analyzed by high-performance liquid chromatography (HPLC).

About 0.01 g of a sample was diluted in about 20 ml of methanol and then measured by HPLC.

Model: Waters e2695

Column: C18 (4.6×250 mm), 5 μm

UV detector: 242 nm

Injection volume: 10 μl

Eluent (gradient) A: $H_2O+H_3PO_4$, B: acetonitrile

Test Example 2: Measurement of Residual Solvents-GC

The content of residual ethylene glycol (EG) in recycled bis(2-hydroxyethyl) terephthalate (BHET) was measured by gas chromatography (GC).

About 0.1 g of a sample was diluted in about 10 ml of $CHCl_3$, treated with a filter of 0.45 μm, and then measured by GC.

Model: Agilent 7890B

Column: DB-624 (30 m×0.25 mm×1.4 μm)

Oven Temp.: 60° C. (2 min.)–10° C./min.–200° C. (0 min.)–20° C./min.–260° C. (5 min.)

Injector temp.: 250° C.

Detector temp.: 250° C.

Flow: 1.5 ml/min. ($N_2$), split ratio: 1/50

Test Example 3: Yellow Index (YID)

Recycled bis(2-hydroxyethyl) terephthalate was mixed with ethylene glycol (EG) and dissolved at 120° C. for 1 hour to obtain a solution having a concentration of 25% by weight. Transmission data for the solution were obtained with Illuminant D65 using Color Flex EZ of Hunterlab at an observer's angle of 2°. The yellow index (YID) value was calculated using a color analyzer in the software.

The test results are shown in Table 1 below.

TABLE 1

| | | r-BHET | | | | |
|---|---|---|---|---|---|---|
| | | A1 | A2 | A3 | A5 | B2 |
| HPLC | BHET* | 98.21 | 98.2 | 97.84 | 96.76 | 84.58 |
| (area %) | MHET* | 1.09 | 1.08 | 1.1 | 1.89 | 2.18 |
| | DEG ester 1* | 0.44 | 0.43 | 0.62 | 0.8 | 5.35 |
| | DEG ester 2* | 0 | 0 | 0.16 | 0.1 | 0.27 |
| | Dimer | 0.2 | 0.19 | 0.22 | 0.23 | 6.36 |
| | Trimer | 0 | 0 | 0 | 0 | 0.72 |
| | Others | 0.06 | 0.1 | 0.06 | 0.22 | 0.54 |
| GC | Residual EG (wt. %) | 0.07 | 0.07 | 0.08 | 0.23 | 0.45 |
| YID | r-BHET solution | 0.59 | 1.23 | 1.56 | 2.38 | 6.7 |

*BHET: bis(2-hydroxyethyl) terephthalate,

*MHET: mono(2-hydroxyethyl) terephthalic acid

*DEG ester 1: 2-hydroxyethyl[2-(2-hydroxyethoxy)ethyl] terephthalate

*DEG ester 2: bis[2-(2-hydroxyethoxy)ethyl]benzene-1,4-dicarboxylate

As can be seen from the above table, in r-BHET_A1 to r-BHET_A5, the ratio of BHET was high, no inorganic impurities were observed, and the content of DEG-derived esters was very low. In contrast, r-BHET_B2 had a problem in that it contained a large amount of dimers or DEG-derived esters and had some residual solvents (EG).

Preparation of an Aqueous Solution of Recycled BHET and Preparation of a Polyester Resin Example 1

Step A: Preparation and Storage of an Aqueous Solution of r-BHET

R-BHET_A2 previously prepared as recycled bis(2-hydroxyethyl) terephthalate was dissolved in water at 87° C., and water was additionally added thereto, or evaporated therefrom, to obtain an aqueous solution having a concentration adjusted to 85% by weight. The aqueous solution of recycled bis(2-hydroxyethyl) terephthalate was stored at the same temperature (87° C.) for 5 days and used as it was in the next step.

Step B: Polymerization of a Polyester Resin

An esterification reactor was charged with the aqueous solution of recycled bis(2-hydroxyethyl) terephthalate obtained in the previous step (r-BHET_A2, 64,677.1 kg), ethylene glycol (EG, 263.1 kg), 1,4-cyclohexanedimethanol (CHDM, 1,833.4 kg), isosorbide (ISB, 495.7 kg), diethylene glycol (DEG, 539.8 kg), a Ge catalyst (32.0 kg), a blue toner (0.150 kg), and a red toner (0.075 kg). Subsequently, nitrogen was injected into the esterification reactor to make the reactor pressurized by 2.0 kgf/cm$^2$ higher than normal pressure (absolute pressure: 2,231.1 mmHg). Then, the temperature of the esterification reactor was raised to 220° C. over 90 minutes and maintained at 220° C. for 2 hours, and the temperature was then raised again to 260° C. over 2 hours. The mixture in the esterification reactor was stored at 260° C. for about 7 hours and then transferred to a polycondensation reactor, and by-products formed during the reaction were discharged through a column and a condenser. Then, the pressure of the polycondensation reactor was reduced from normal pressure to 5 Torr (absolute pressure: 5 mmHg) over 30 minutes. At the same time, the temperature of the polycondensation reactor was raised to 280° C. over 1 hour, and a polycondensation reaction was then carried out while the pressure of the polycondensation reactor was maintained at 1 Torr (absolute pressure: 1 mmHg) or less. At the beginning of the polycondensation reaction, the stirring speed may be set high. As the polycondensation reaction proceeds, when the stirring power is weakened due to the increase in the viscosity of the reactants or the temperature of the reactants rises above the set temperature, the stirring speed may be appropriately adjusted accordingly. The polycondensation reaction was carried out until the intrinsic viscosity (IV) of the mixture (melt) in the reactor reached 0.70 dl/g. When the intrinsic viscosity of the mixture in the reactor reached the desired level, the mixture was then discharged to the outside of the reactor to form pellets, which were solidified with a cooling liquid and then granulated to have an average weight of about 12 to 14 mg to prepare about 50 tons of a polyester resin (copolymer).

Example 2

The same procedure as in Example 1 was repeated to obtain about 50 tons of a polyester resin (copolymer), except that, in step A, r-BHET_A3 was used as recycled bis(2-hydroxyethyl)terephthalate, the dissolution temperature was 90° C., and the concentration was 80% by weight; and that, in step B, the reactor was charged with the aqueous solution of recycled bis(2-hydroxyethyl) terephthalate (r-BHET_A3, 32,424.4 kg), terephthalic acid (TPA, 21,190.8 kg), ethylene glycol (EG, 8,389.5 kg), 1,4-cyclohexanedimethanol (CHDM, 735.3 kg), diethylene glycol (DEG, 1,353.1 kg), a Ge catalyst (32.0 kg), a Ti catalyst (4.5 kg), phosphoric acid (5.0 kg), a blue toner (0.200 kg), and a red toner (0.050 kg), the esterification reaction was carried out at a temperature of 260° C. and a pressure higher than normal pressure by 0.5 kgf/cm$^2$, and the polycondensation reaction was carried out at a temperature of 275° C. until the intrinsic viscosity (IV) reached 0.78 dl/g.

Example 3

The same procedure as in Example 1 was repeated to obtain about 50 tons of a polyester resin (copolymer), except that, in step A, r-BHET_A5 was used as recycled bis(2-hydroxyethyl)terephthalate, the dissolution temperature was 110° C., and the concentration was 95% by weight; and that, in step B, the reactor was charged with the aqueous solution of recycled bis(2-hydroxyethyl) terephthalate (r-BHET_A5, 49,265.2 kg), terephthalic acid (TPA, 5,681.8 kg), ethylene glycol (EG, 707.4 kg), 1,4-cyclohexanedimethanol (CHDM, 10,514.8 kg), a CHDM derivative (comprising 4-(hydroxymethyl)cyclohexylmethyl-4-(hydroxymethyl)cyclohexanecarboxylate and 4-(4-(hydroxymethyl)cyclohexylmethoxymethyl)cyclohexylmethanol at a molar ratio of 1:3, 999.5 kg), a Ge catalyst (64.0 kg), a Ti catalyst (4.5 kg), phosphoric acid (5.0 kg), cobalt acetate (6.3 kg), a blue toner (0.030 kg), and a red toner (0.010 kg), the esterification reaction was carried out at a temperature of 255° C. and a pressure higher than normal pressure by 2.0 $kgf/cm^2$, and the polycondensation reaction was carried out at a temperature of 285° C. until the intrinsic viscosity (IV) reached 0.78 dl/g.

Example 4

The same procedure as in Example 1 was repeated to obtain about 50 tons of a polyester resin (copolymer), except that, in step A, r-BHET_A1 was used as recycled bis(2-hydroxyethyl)terephthalate, the dissolution temperature was 60° C., and the concentration was 70% by weight; and that, in step B, the reactor was charged with the aqueous solution of recycled bis(2-hydroxyethyl) terephthalate (r-BHET_A1, 17,210.2 kg), terephthalic acid (TPA, 26,244.5 kg), ethylene glycol (EG, 9,662.1 kg), 1,4-cyclohexanedimethanol (CHDM, 10,082.2 kg), diethylene glycol (DEG, 2,394.1 kg), a Ti catalyst (0.9 kg), phosphoric acid (10.0 kg), cobalt acetate (13.7 kg), a blue toner (0.030 kg), and a red toner (0.010 kg), the esterification reaction was carried out at a temperature of 250° C. and a pressure higher than normal pressure by 1.5 $kgf/cm^2$, and the polycondensation reaction was carried out at a temperature of 270° C. until the intrinsic viscosity (IV) reached 0.82 dl/g.

Example 5

The same procedure as in Example 1 was repeated to obtain about 50 tons of a polyester resin (copolymer), except that, in step A, r-BHET_A5 was used as recycled bis(2-hydroxyethyl)terephthalate, the dissolution temperature was 80° C., and the concentration was 50% by weight; and that, in step B, the reactor was charged with the aqueous solution of recycled bis(2-hydroxyethyl) terephthalate obtained in the previous step (r-BHET_A5, 13,403.4 kg), terephthalic acid (TPA, 26,279.1 kg), 1,4-cyclohexanedimethanol (CHDM, 19,756.8 kg), isosorbide (ISB, 6,163.5 kg), diethylene glycol (DEG, 2,237.4 kg), a Ge catalyst (320.2 kg), phosphoric acid (1.0 kg), a blue toner (0.150 kg), and a red toner (0.050 kg), the esterification reaction was carried out at a temperature of 265° C. and a pressure higher than normal pressure by 1.0 $kgf/cm^2$, and the polycondensation reaction was carried out at a temperature of 275° C. until the intrinsic viscosity (IV) reached 0.70 dl/g.

Example 6

The same procedure as in Example 1 was repeated to obtain about 50 tons of a polyester resin (copolymer), except that, in step A, r-BHET_A3 was used as recycled bis(2-hydroxyethyl)terephthalate, the dissolution temperature was 90° C., and the concentration was 60% by weight; and that, in step B, the reactor was charged with the aqueous solution of recycled bis(2-hydroxyethyl) terephthalate obtained in the previous step (r-BHET_A3, 5,438.2 kg), terephthalic acid (TPA, 35,935.9 kg), ethylene glycol (EG, 9,882.0 kg), 1,4-cyclohexanedimethanol (CHDM, 2,740.5 kg), diethylene glycol (DEG, 2773.8 kg), a CHDM derivative (comprising 4-(hydroxymethyl)cyclohexylmethyl-4-(hydroxymethyl)cyclohexanecarboxylate and 4-(4-(hydroxymethyl)cyclohexylmethoxymethyl)cyclohexylmethanol at a molar ratio of 1:3, 2,083.9 kg), a Ge catalyst (32.0 kg), phosphoric acid (5.0 kg), a blue toner (0.250 kg), and a red toner (0.100 kg), the esterification reaction was carried out at a temperature of 260° C. and a pressure higher than normal pressure by 0.5 $kgf/cm^2$, and the polycondensation reaction was carried out at a temperature of 275° C. until the intrinsic viscosity (IV) reached 0.75 dl/g.

Example 7

The same procedure as in Example 1 was repeated, except that, in step A, r-BHET_A5 was used as recycled bis(2-hydroxyethyl)terephthalate, the dissolution temperature was 105° C., and the concentration was 90% by weight; and that, in step B, the reactor was charged with the aqueous solution of recycled bis(2-hydroxyethyl) terephthalate obtained in the previous step (r-BHET_A5, 45,274.0 kg), terephthalic acid (TPA, 12,680.8 kg), isophthalic acid (IPA, 29,588.5 kg), ethylene glycol (EG, 9,261.9 kg), 1,4-cyclohexanedimethanol (CHDM, 1,833.4 kg), isosorbide (ISB, 495.7 kg), diethylene glycol (DEG, 1,349.6 kg), a Ti catalyst (4.5 kg), phosphoric acid (1.0 kg), cobalt acetate (8.5 kg), a blue toner (0.250 kg), and a red toner (0.100 kg), the esterification reaction was carried out at a temperature of 260° C. and a pressure higher than normal pressure by 3.0 $kgf/cm^2$ until the intrinsic viscosity (IV) reached 0.65 dl/g, and the polycondensation reaction was carried out at a temperature of 280° C. to obtain granules. The granules were left at 150° C. for 1 hour to be crystallized, which were then fed to a solid-state polymerization reactor. While nitrogen flowed at a rate of 50 L/minute, the temperature of the reactor was raised from room temperature to 190° C. at a rate of 40° C./hour. While it was maintained, a solid-state polymerization was carried out until the intrinsic viscosity (IV) of the granules in the reactor reached 1.10 dl/g to obtain about 50 tons of a polyester resin (copolymer).

Comparative Example 1

The same procedure as in Example 7 was repeated, except that, in step A, r-BHET_A5 was used as recycled bis(2-hydroxyethyl)terephthalate, the dissolution temperature was 120° C., and the concentration was 50% by weight; and that, in step B, the reactor was charged with the aqueous solution of recycled bis(2-hydroxyethyl) terephthalate obtained in the previous step (r-BHET_A5, 26,318.5 kg), terephthalic acid (TPA, 25,800.4 kg), ethylene glycol (EG, 10,707.0 kg), 1,4-cyclohexanedimethanol (CHDM, 746.0 kg), isosorbide (ISB, 504.3 kg), a Ge catalyst (64.0 kg), a blue toner (0.150 kg), and a red toner (0.050 kg), the esterification reaction was carried out at a temperature of 260° C. and a pressure higher than normal pressure by 0.5 $kgf/cm^2$, the polycondensation reaction was carried out at a temperature of 280° C. until the intrinsic viscosity (IV) reached 0.50 dl/g, and the solid-state polymerization was carried out at a temperature of 200° C. until the intrinsic viscosity (IV) reached 0.70 dl/g to obtain about 50 tons of a polyester resin (copolymer).

Comparative Example 2

The same procedure as in Example 7 was repeated, except that, in step A, r-BHET_B2 was used as recycled bis(2- hydroxyethyl)terephthalate, which was melted at 130° C., without mixing with water, to prepare liquid recycled bis (2-hydroxyethyl) terephthalate (concentration: 100% by weight); and that, in step B, the reactor was charged with the liquid recycled bis(2-hydroxyethyl) terephthalate obtained in the previous step (r-BHET_B2, 19,107.3 kg), terephthalic acid (TPA, 29,137.4 kg), ethylene glycol (EG, 27,413.9 kg), 1,4-cyclohexanedimethanol (CHDM, 3,610.8 kg), isosorbide (ISB, 976.3 kg), diethylene glycol (DEG, 265.8 kg), a Ti catalyst (1.8 kg), cobalt acetate (8.5 kg), a blue toner (0.150 kg), and a red toner (0.050 kg), the esterification reaction was carried out at a temperature of 260° C. and a pressure higher than normal pressure by 1.0 kgf/$cm^2$, the polycondensation reaction was carried out at a temperature of 280° C. until the intrinsic viscosity (IV) reached 0.70 dl/g, and the solid-state polymerization was carried out at a temperature of 200° C. until the intrinsic viscosity (IV) reached 0.95 dl/g to obtain about 50 tons of a polyester resin (copolymer).

Comparative Example 3

The same procedure as in Example 1 was repeated to obtain about 50 tons of a polyester resin (copolymer), except that, in step A, r-BHET_A1 was used as recycled bis(2-hydroxyethyl)terephthalate, the dissolution temperature was 50° C., and the concentration was 40% by weight; and that, in step B, the reactor was charged with the aqueous solution of recycled bis(2-hydroxyethyl) terephthalate obtained in the previous step (r-BHET_A1, 64,677.1 kg), ethylene glycol (EG, 263.1 kg), 1,4-cyclohexanedimethanol (CHDM, 1,833.4 kg), isosorbide (ISB, 495.7 kg), diethylene glycol (DEG, 539.8 kg), a Ge catalyst (320.2 kg), phosphoric acid (1.0 kg), a blue toner (0.150 kg), and a red toner (0.050 kg), the esterification reaction was carried out at a temperature of 255° C. and a pressure higher than normal pressure by 0.5 kgf/$cm^2$, and the polycondensation reaction was carried out at a temperature of 280° C. until the intrinsic viscosity (IV) reached 0.60 dl/g.

Test Example 4: Changes in r-BHET Composition

Aqueous solutions of recycled BHET were each prepared in the same manner as in step A of the Examples and Comparative Examples, which was stored for 5 days while the temperature was maintained. Thereafter, the solvent (water) in the aqueous solution was evaporated, and HPLC analysis was performed in the same manner as in Test Example 1 above. The peak area fractions (%) of BHET and dimers thus analyzed are shown in Tables 2 and 3 below.

In addition, the difference from the initial peak area fraction (%) of BHET shown in Table 1 above was calculated, and the change in purity (ABHET) after storage for 5 days as an aqueous solution was calculated.

$$\Delta BHET = BHET\,(\text{day } 0) - BHET\,(\text{day } 5)$$

Here, BHET (day 0) is the peak area fraction (%) of BHET in the HPLC result of recycled BHET obtained by depolymerization, and BHET (day 5) is the peak area fraction (%) after storage for 5 days as an aqueous solution.

Test Example 5: Change in Yellow Index (YID)

Aqueous solutions of recycled BHET were each prepared in the same manner as in step A of the Examples and Comparative Examples, which was stored for 5 days while the temperature was maintained. Thereafter, the water in the aqueous solution was evaporated to obtain recycled BHET powder, which was measured for yellow index (YID) in the same manner as in Test Example 3. The results are shown in Tables 2 and 3 below.

In addition, the difference from the initial yellow index shown in Table 1 above was calculated, and the change in the yellow index (ΔYID) after storage for 5 days was calculated.

$$\Delta YID = YID\,(\text{day } 5) - YID\,(\text{day } 0)$$

Here, YID (day 0) is the yellow index measured for recycled BHET obtained by depolymerization, and YID (day 5) is the yellow index measured for recycled BHET after storage for 5 days as an aqueous solution.

The test results are shown in the tables below.

TABLE 2

| r-BHET type | | Ex. 1 A2 | Ex. 2 A3 | Ex. 3 A5 | Ex. 4 A1 | Ex. 5 A5 |
|---|---|---|---|---|---|---|
| Aq. solution of r-BHET | Dissolution temp. (° C.) | 87 | 90 | 110 | 60 | 80 |
| | Conc. (% by weight) | 85 | 80 | 95 | 70 | 50 |
| HPLC after 5 days (area %) | BHET (day 5) | 96.86 | 96.23 | 91.83 | 98.21 | 96.76 |
| | ΔBHET | 0.55 | 2.34 | 4.90 | 0.20 | 0.23 |
| | Dimer | −1.34 | −1.61 | −4.93 | 0.00 | 0.00 |
| YID after 5 days | YID (day 5) | 2.14 | 2.68 | 4.87 | 0.84 | 3.33 |
| | ΔYID | 0.91 | 1.12 | 2.49 | 0.25 | 0.95 |

TABLE 3

| r-BHET type | | Ex. 6 A3 | Ex. 7 A5 | C. Ex. 1 A5 | C. Ex. 2 B2 | C. Ex. 3 A1 |
|---|---|---|---|---|---|---|
| Aq. solution of r-BHET | Dissolution temp. (° C.) | 90 | 105 | 120 | 130 | 50 |
| | Conc. (% by weight) | 60 | 90 | 50 | 100 | 40 |
| HPLC after 5 days (area %) | BHET (day 5) | 96.23 | 92.99 | 89.51 | 67.50 | 98.21 |
| | ΔBHET | 0.22 | 4.12 | 7.05 | 20.00 | 0.20 |
| | Dimer | −1.61 | −3.77 | −7.25 | −17.08 | 0.00 |
| YID after 5 days | YID (day 5) | 2.40 | 4.63 | 5.24 | 15.41 | 0.71 |
| | ΔYID | 0.84 | 2.25 | 2.86 | 8.71 | 0.12 |

Test Example 6: Evaluation of Resin Color

The chromaticity and brightness of samples were measured using a Varian Cary 5 UV/Vis/NIR spectrophotometer equipped with a diffuse reflection accessory. A polyester resin specimen with a thickness of 6 mm was prepared, for which transmission data with Illuminant D65 at an observer's angle of 2° were obtained and processed using a color analyzer in Grams/32 software to calculate Hunter Lab values. The results of subtracting the b value from the L value (L−b) are shown in the table below.

The test results are shown in Tables 4 and 5 below. The composition of each polyester resin prepared in each Example and Comparative Example was also shown together.

TABLE 4

| r-BHET content (wt. %) | | Ex. 1 95 | Ex. 2 78 | Ex. 3 68 | Ex. 4 46 | Ex. 5 17 |
|---|---|---|---|---|---|---|
| Molar ratio of monomers | r-BHET | 254.6 | 127.7 | 194.0 | 67.8 | 52.8 |
| | TPA | 0.0 | 127.7 | 34.2 | 158.1 | 158.3 |
| | EG | 4.2 | 135.3 | 11.4 | 155.8 | 0.0 |
| | DEG | 5.1 | 12.8 | 0.0 | 22.6 | 21.1 |
| | CHDM | 12.7 | 5.1 | 73.0 | 70.0 | 137.2 |
| | CHDM derivative | 0.0 | 0.0 | 3.7 | 0.0 | 0.0 |
| | ISB | 3.4 | 0.0 | 0.0 | 0.0 | 42.2 |
| Color | Hunter L − b | 92 | 85 | 87 | 89 | 87 |

TABLE 5

| r-BHET content (wt. %) | | Ex. 6 10 | Ex. 7 66 | C. Ex. 1 44 | C. Ex. 2 27 | C. Ex. 3 96 |
|---|---|---|---|---|---|---|
| Molar ratio of monomers | r-BHET | 21.4 | 178.2 | 103.6 | 75.2 | 254.6 |
| | TPA | 216.5 | 76.4 | 155.4 | 175.5 | 0.0 |
| | EG | 159.4 | 149.4 | 172.7 | 442.2 | 4.2 |
| | DEG | 26.2 | 12.7 | 0.0 | 2.5 | 5.1 |
| | CHDM | 19.0 | 12.7 | 5.2 | 25.1 | 12.7 |
| | CHDM derivative | 7.8 | 0.0 | 0.0 | 0.0 | 0.0 |
| | ISB | 0.0 | 3.4 | 3.5 | 6.7 | 3.4 |
| Color | Hunter L − b | 86 | 91 | 80 | 76 | 84 |

Referring to the results of the Examples, Comparative Examples, and their Test Examples, when recycled bis(2-hydroxyethyl) terephthalate was prepared as an aqueous solution under the preferred ranges of dissolution temperature and concentration of the present invention and stored as in Examples 1 to 7, the change in purity and yellow index even after 5 days was very small, and the color quality of the polyester resins prepared therefrom was excellent as well.

In contrast, when it was not stored as an aqueous solution or stored as an aqueous solution outside the preferred ranges of dissolution temperature and concentration range as in Comparative Examples 1 to 3, the change in purity and yellow index after 5 days was very large, or the color quality of the polyester resins prepared therefrom was poor.

The invention claimed is:

1. A process for preparing a polyester resin, which comprises:

(1) depolymerizing waste polyester to prepare recycled bis(2-hydroxyethyl) terephthalate;

(2) mixing the recycled bis(2-hydroxyethyl) terephthalate with water at 60° C. to 110° C. to prepare an aqueous solution of recycled bis(2-hydroxyethyl) terephthalate having a concentration of 50% by weight to 95% by weight, wherein the concentration is the weight of the recycled bis(2-hydroxyethyl) terephthalate based on the total weight of the aqueous solution of recycled bis(2-hydroxyethyl) terephthalate; and (3) preparing a polyester resin through an esterification reaction and a polycondensation reaction using the aqueous solution of recycled bis(2-hydroxyethyl) terephthalate, wherein a change in yellow index (ΔYID) calculated by following equation is 6 or less:

$$\Delta YID = YID\ (day\ 5) - YID\ (day\ 0)$$

wherein:

YID (day 5) is a yellow index (YID) value measured when recycled bis(2-hydroxyethyl) terephthalate obtained by storing the aqueous solution of recycled bis(2-hydroxyethyl) terephthalate prepared in step (2) at 60° C. to 110° C. for 5 days and then evaporating water is dissolved in ethylene glycol at a concentration of 25% by weight at 120° C. for 1 hour, YID (day 0) is a yellow index (YID) value measured when recycled bis(2-hydroxyethyl) terephthalate prepared in step (1) is dissolved in ethylene glycol at a concentration of 25% by weight at 120° C. for 1 hour, and the yellow index (YID) value is calculated using a color analyzer based on transmission data for a solution obtained with Illuminant D65 using Color Flex EZ of Hunterlab at an observer's angle of 2°.

2. The process for preparing a polyester resin of claim 1, wherein step (1) comprises:

(1a) subjecting waste polyester to depolymerization by a first glycolysis reaction at a temperature of 180° C. to 200° C. to obtain a first reactant;

(1b) subjecting the first reactant to depolymerization by a second glycolysis reaction at a temperature of 150° C. to 170° C. to obtain a second reactant;

(1c) subjecting the second reactant to ion exchange through an ion-exchange resin to obtain a third reactant;

(1d) removing an unreacted glycol from the third reactant through distillation at a temperature of 150° C. or lower to obtain a fourth reactant; and (1e) subjecting the fourth reactant to distillation to obtain crude bis(2-hydroxyethyl) terephthalate.

3. The process for preparing a polyester resin of claim 1, wherein the recycled bis(2-hydroxyethyl) terephthalate has a peak area fraction of bis(2-hydroxyethyl) terephthalate of 96% or more and a peak area fraction of 2-hydroxyethyl[2-(2-hydroxyethoxy)ethyl] terephthalate of 2.5% or less, when measured by high-performance liquid chromatography (HPLC).

4. The process for preparing a polyester resin of claim 1, wherein step (2) comprises:

(2a) mixing the recycled bis(2-hydroxyethyl) terephthalate with water at 60° C. to 110° C.; and (2b) adjusting the concentration to 50% by weight to 95% by weight through further addition or evaporation of water after the mixing.

5. The process for preparing a polyester resin of claim 1, wherein, when recycled bis(2-hydroxyethyl) terephthalate obtained by storing the aqueous solution of recycled bis(2-hydroxyethyl) terephthalate prepared in step (2) at 60° C. to 110° C. for 5 days and then evaporating water is dissolved in ethylene glycol at a concentration of 25% by weight at 120° C. for 1 hour, the yellow index (YID) is measured to be 5 or less.

6. The process for preparing a polyester resin of claim 1, wherein, when the aqueous solution of recycled bis(2-hydroxyethyl) terephthalate prepared in step (2) is stored at 60° C. to 110° C. for 5 days, the purity of the recycled BHET is measured to have a difference of 5% or less from the initial purity.

7. The process for preparing a polyester resin of claim 1, wherein at least one monomer selected from the group consisting of (a) a dicarboxylic acid or a derivative thereof, (b) ethylene glycol or diethylene glycol, and (c) a diol-based comonomer is further introduced into the esterification reaction.

8. The process for preparing a polyester resin of claim 7, wherein the dicarboxylic acid comprises at least one selected from terephthalic acid and isophthalic acid.

9. The process for preparing a polyester resin of claim 7, wherein the diol-based comonomer comprises at least one selected from the group consisting of cyclohexanedimethanol, cyclohexanedimethanol derivatives, and isosorbide.

10. The process for preparing a polyester resin of claim 9, wherein the cyclohexanedimethanol derivative is 4-(hydroxymethyl)cyclohexylmethyl-4-(hydroxymethyl)cyclohexanecarboxylate or 4-(4-(hydroxymethyl)cyclohexylmethoxymethyl)cyclohexylmethanol.

11. The process for preparing a polyester resin of claim 7, wherein the diol-based comonomer further comprises 1,2-propanediol, 1,3-propanediol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 1,4-butanediol, 2,3-butanediol, 3-methyl-1,5-pentanediol, 3-methyl-2,4-pentanediol, 1,6-hexanediol, 1,2-cyclohexanediol, and 1,4-cyclohexanediol.

12. The process for preparing a polyester resin of claim 1, wherein the polyester resin has a value obtained by subtracting the b value from the L value of 85 or more when Hunter Lab color space is measured.

13. A process for preparing an aqueous solution of recycled bis(2-hydroxyethyl) terephthalate, which comprises:

(1) depolymerizing waste polyester to prepare recycled bis(2-hydroxyethyl) terephthalate; and (2) mixing the recycled bis(2-hydroxyethyl) terephthalate with water at 60° C. to 110° C. to prepare an aqueous solution thereof having a concentration of 50% by weight to 95% by weight, wherein the concentration is the weight of the recycled bis(2-hydroxyethyl) terephthalate based on the total weight of the aqueous solution of recycled bis(2-hydroxyethyl) terephthalate, wherein a change in yellow index (ΔYID) calculated by following equation is 6 or less:

$$\Delta YID = YID\ (day\ 5) - YID\ (day\ 0)$$

wherein:

YID (day 5) is a yellow index (YID) value measured when recycled bis(2-hydroxyethyl) terephthalate obtained by storing the aqueous solution of recycled bis(2-hydroxyethyl) terephthalate prepared in step (2) at 60° C. to 110° C. for 5 days and then evaporating water is dissolved in ethylene glycol at a concentration of 25% by weight at 120° C. for 1 hour, YID (day 0) is a yellow index (YID) value measured when recycled bis(2-hydroxyethyl) terephthalate prepared in step (1) is dissolved in ethylene glycol at a concentration of 25% by weight at 120° C. for 1 hour, and the yellow index (YID) value is calculated using a color analyzer based on transmission data for a solution obtained with Illuminant D65 using Color Flex EZ of Hunterlab at an observer's angle of 2°.

* * * * *